United States Patent [19]

Selker

[11] Patent Number: 4,957,115

[45] Date of Patent: Sep. 18, 1990

[54] DEVICE FOR DETERMINING THE PROBABILITY OF DEATH OF CARDIAC PATIENTS

[75] Inventor: Harry P. Selker, Wellesley, Mass.

[73] Assignee: New England Medical Center Hosp., Boston, Mass.

[21] Appl. No.: 173,220

[22] Filed: Mar. 25, 1988

[51] Int. Cl.⁵ .............................................. A61B 5/04
[52] U.S. Cl. .................................. 128/696; 364/413.06
[58] Field of Search ............................... 128/695–696, 128/702–705; 364/413.06

[56] References Cited

U.S. PATENT DOCUMENTS 4,679,144  7/1987  Cox et al. ..................... 128/702 X
4,680,708  7/1987  Anbos et al. ................. 128/702 X

OTHER PUBLICATIONS

Harvey, W.P. et al., editors "Yearbook of Cardiology," 1985, pp. 170–173 (copy 128/335).
Pozen et al., "A Predictive Instrument to Improve Coronary-Care Unit Admission Practices in Acute Ischemic Heart Disease", N.E. Journal of Medicine 310:1273–1278 (May 1984).

*Primary Examiner*—Francis Jaworski

[57] ABSTRACT

A device for determining the probability of death in cardiovascular patients including an electrocardiograph adapted to deliver a signal in the form of an electrical waveform containing information about the condition of the patient's heart; a waveform recognition and measurement device adapted to analyze the waveform and generate output based on the analysis; and a computer adapted to receive the output and calculate a numerical value representing the probability based on the output. Also provided is a method for assessing cardiovascular mortality risk at a health care facility or provider using this device.

22 Claims, 3 Drawing Sheets

Probability of Death = 100 X $\{1-1/(1+\exp(b_0+\Sigma b_i x_i)\}$

MI MORTALITY PREDICTOR

| Variable | Coefficient | | Values(x) |
|---|---|---|---|
| CONSTANT | ($b_O$) -9.343 | | |
| AGE | 0.079 | Age at last birthday | Age |
| STUP1 | 0.849 | ECG ST-segment elevated 1mm<br>Otherwise | 1<br>0 |
| STUP2 | 1.054 | ECG ST-segment elevated 2mm<br>Otherwise | 1<br>0 |
| STLESS1 | 0.373 | ECG ST-segment depressed 1 mm<br>Otherwise | 1<br>0 |
| STLESS2 | 0.780 | ECG ST-segment depressed 2mm<br>Otherwise | 1<br>0 |
| TWUP | 1.097 | ECG T-waves elevated<br>Otherwise | 1<br>0 |
| TWINV2 | 0.478 | ECG T-waves depressed<br>Otherwise | 1<br>0 |
| QAALMI | 0.343 | ECG Q-waves anterior or anteriorlateral<br>Otherwise | 1<br>0 |
| HRBPLOW | 3.444 | Heart Rate 0-10 and<br>Systolic Blood Pressure 0-10<br>Otherwise | 1<br>0 |
| HRGT100 | 0.569 | Heart Rate >100<br>Otherwise | 1<br>0 |
| SBP1190 | 3.267 | Systolic Blood Pressure 11-90<br>Otherwise | 1 |
| SBP91140 | 1.483 | Systolic Blood Pressure 91-140<br>Otherwise | 1<br>0 |

FIG. 3

SEVERITY - CHF PREDICTOR

| Variable | Coefficient | | Values (x) |
|---|---|---|---|
| CONSTANT ($b_0$) | -10.1990 | | |
| AGE | 0.0944 | Age at last birthday | Age |
| SBP090 | 1.5238 | Systolic Blood Pressure 0-90 | 1 |
| | | Otherwise | 0 |
| SBP91100 | 2.2324 | Systolic Blood Pressure 91-100 | 1 |
| | | Otherwise | 0 |
| LVHESTES | -2.4268 | Left Ventricular Hypertrophy | 1 |
| | | Otherwise | 0 |

FIG. 4

DEVICE FOR DETERMINING THE PROBABILITY OF DEATH OF CARDIAC PATIENTS

BACKGROUND OF THE INVENTION

The invention relates to an electrocardiograph device that determines a patient's probability of death from cardiovascular disease.

In the United States, approximately 4.5 million patients per year enter emergency rooms (ERs) with symptoms suggesting accute cardiac disease, and of those, one third are subsequently admitted to Coronary Care Units (CCUs). A physician must decide whether triage options other than the CCU (e.g., intermediate care units, ward beds, observation units, or home care under close supervision) may be more appropriate. In addition to the patient's condition, to the extent it can be accurately assesed, other factors to be considered include the scarcity of facilities, continually increasing costs, and the new stricter cost containment strategies (e.g. diagnostic related groups (DRGs)). Such decisions are difficult because they require an accurate, reliable determination of a patient's true level of risk, and such determinations are themselves difficult to perform.

Hospitals currently release mortality data (i.e. the fraction of patients who die per year) that are not adjusted in accordance with differences in their respective patient populations. If such data are to be used as metrics of quality of medical care, these data should be calibrated in order to facilitate fair comparisons between hospitals with different patient populations.

In Pozen, et al. New Enqland J. of Med. 310, 1273-1278, 1984, a hand-held calculator was programmed to provide the emergency room physician with a patient's calculated likelihood of having acute ischemia. Its use depends on the physician's interpretation of the patient's ECG. It uses a logistic regression function with coeficients derived by stepwise regression analysis.

Electrocardiographs exist that imitate physician judgment by using feature recognition algorithms in conjunction with a rule based computer program to provide a qualitative diagnosis of a patient's condition.

Other electrocardiographs exist that use feature recognition data and feature measurements as inputs to a logistic regression formula to provide a quantitative measure of the possibility of ischemia (a type of heart attack).

The probability of ischemia is not the same as the probability of death, because there are other causes of acute and dangerous cardiac conditions. For example, a patient with new or unstable angina pectoris has approximately a 5 percent chance of dying, whereas a patient with a Killip Class IV myocardial infarction has an approximately 80 per cent chance of death. This is important because it is the probability of death, not the probability of ischemia, that is critical to a physician's triage decision.

SUMMARY

In general the invention features a device for determining the probability of death in cardiovascular patients that includes an electrocardiograph adapted to deliver a signal in the form of an electrical waveform containing information about the condition of the patient's heart, a waveform recognition and measurement device adapted to analyze the waveform and generate output based on the analysis, and a computer adapted to receive the output and calculate a numerical value representing the probability based on the output.

In preferred embodiments, the cardiovascular patient is primarily at risk for mortality due to acute myocardial infarction, or heart failure.

Another general feature of the invention is a method for assessing cardiovascular mortality risk at a health care facility or provider that includes the steps of providing the device of the invention to the health care facility or provider, using the device to calculate an individual predicted cardiovascular mortality risk of a patient at the health care facility or provider, repeating this last step for a large number of the patients, and using the individual predicted cardiovascular mortality risks to calculate a collective predicted cardiovascular mortality risk, and adjusting the collective observed cardiovascular mortality rate for the facility or provider using the collective predicted cardiovascular mortality risk to yield a summary statistic representing the overall mortality risk at the facility or provider, or the risk adjusted mortality rate at the facility or provider.

In preferred embodiments, the individual predicted cardiovascular mortality risks conform substantially to a normal distribution, and may be characterized by a mean, called the collective predicted cardiovascular mortality risk, and a variance, and wherein the adjusted collective cardiovascular mortality rate is calculated by dividing the collective observed cardiovascular mortality risk by the collective predicted cardiovascular mortality risk, and multiplying the ratio so formed by a reference mortality rate, which may be a national statistic, or may be a regional or local statistic.

The invention allows fair comparisons between hospitals with different patient populations.

The invention facilitates clinicians' positive involvement by its ease of use, and by providing measures of risk that are sufficiently accurate, reliable, and immediate to be of value in the real-time clinical setting. The immediacy of the assessment allows the accurate capture of a patient's true presenting mortality risk, not a risk that was assessed after a 24-hour or longer delay, as is the current predominant practice, during which time increased severity might in fact be due to poor quality care.

The invention helps to avoid the need for inappropriate high-technology or special tests. Thus, the patient is spared the added risk and expense of such tests.

The invention maintains objective assessment regardless of where the patient is admitted, whether it's to intensive care or a ward bed, or whether the patient is not admitted at all.

The entire assessment of mortality risk-adjustment can be done without ever looking at actual medical records. The required data, and the risk-adjusted individual predicted cardiovascular mortality rate, could be obtained directly from the electrocardiograph of the invention. Thus, the speed of capture, reliability, and accuracy of the data are all improved, while the cost of data capture is significantly reduced.

Other advantages and features will become apparent from the following description of the preferred embodiment, and from the claims.

DESCRIPTION OF THE PREFERRED EMBODIMENT

We first briefly describe the drawings.

FIG. 3 is a table of logistic regression variables, coefficients and values for the prediction of mortality from myocardial infarction.

FIG. 4 is a table of logistic regression variables, coefficients and values for the prediction of mortality from congestive heart failure.

STRUCTURE

Figures 1, 2:
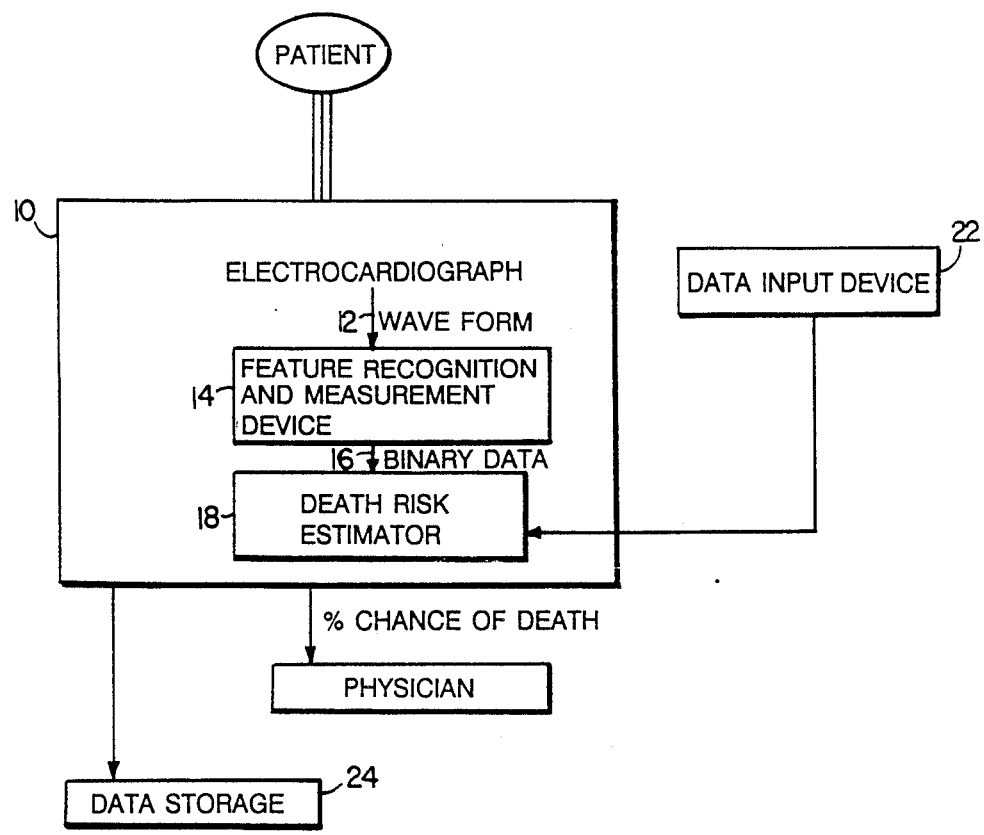
FIG. 1 is a schematic diagram of the electrocardiograph of the invention.
FIG. 2 is a logistic regression formula.

Referring to FIG. 1, a computer assisted electrocardiograph (ECG) (available e.g., from Hewlett Packard Corp.) 10 monitors a patient's cardiac activity. There are twelve electrodes attached to the patient, each monitoring a different portion of the heart. The ECG 10 sends twelve corresponding signals via a lead 12 to a feature recognition and measurement device 14 that decides whether particular critical features are present in each ECG signal (e.g. presence or absence of a Q-wave), and measures the magnitude of other critical features (e.g. extent of ST-segment deperession). These data are digitally encoded in a signal that is received by an additional feature of ECG 10, modified to act as a death risk estimator 18. The death risk estimator 18 is a microcomputer that has been programmed to use the information produced by the feature recognition and measurement device 14, and using a logistic regression formula as in FIG. 2, calculates the quantitative probability value that reflects the likelihood of dying.

Referring to FIG. 2, the logistic regression formula is of the form $P = 100 \times [1 - (1 + e^Y)^{-1}]$, where $Y = b_0 + \Sigma b_i X_i$, where P is a cardiovascular patient's probability of dying expressed as a value ranging from 0.0 to 100.0, e is the base of the natural log; $b_0$ is a constant; $b_i$ is a regression coefficient or weight corresponding to each clinical variable; and $X_i$ is set equal to one if the corresponding clinical variable condition is present, and zero otherwise.

Referring to FIG. 3, variables $X_i$ have been computed using stepwise regression analysis of reference population data using the SAS institute s LOGIST logistic regression computer program. (See Walker, et al. Biometrika 54, 167-79, 1967, and Cary, N. C., SUGI supplement library user's guide, SAS Institute, 181-202, 1983.).

The death risk estimator 18 also prompts the physician for vital signs, such as heart rate and blood pressure, and basic clinical data, such as age and patient complaints. The physician uses a patient data input device 22 to provide this information to the computer.

The ECG waveform, the values $X_i$ computed by the feature recognition and measurement device 14, and the calculated probability of death P, are stored in a database maintained by a data storage unit 24. This data storage unit may then be polled remotely using telecommunications by a central computer for the purpose of compiling mortality statistics of a large population.

Use

There are two applications of the invention: (1) as a clinical tool to be used by physicians and other health care providers in administering care to individual patients, and (2) as a way to collect data on groups of patients to asses the medical care of a provider, provider group or institution, for purposes such as quality assessment, or reimbursement.

In a clinical setting, the electrocardiograph of the invention is used to provide the physician with the patient's risk of dying. This information is used as an aid in the triage decision making process. This information would be used to supplement a physician's or other clinician's judgment, and other available diagnostic information (e.g. patient's symptoms, physical exam and lab data, including the electrocardiogram itself). For example, in an emergency room setting, a patient with a low probability P would be admitted to a ward bed, or not hospitalized.

In addition to aiding in triage decisions, the invention may also help to determine treatment options.

To use the invention for the second application, data must first be collected, including each cardiovascular patient's risk of dying, which can be expressed as a single numerical value P. These values are combined by averaging to yield a collective predicted cardiovascular mortality risk. The collective observed cardiovascular mortality risk is calculated by dividing the total number of those who have died in a health care facility or provider by the total number of those patients who enter the facility or provider with cardiac complaints. To calculate the adjusted collective mortality risk, the ratio of the collective observed cardiovascular mortality to the collective predicted cardiovascular mortality risk is multiplied by a reference mortality rate. This reference mortality rate may be a national statistic, or one of a more local nature. The adjusted collective mortality risk of a facility or health care provider (e.g., an HMO) may then be compared fairly with similarly computed risk values from other facilities or health care providers with different patient populations.

Other modifications and variations will occur to those skilled in the art that are nevertheless within the spirit and scope of the invention as claimed.

I claim:

1. A device for determining the probability of imminent death of a patient from cardiovascular disease comprising:
    a. an electrocardiograph adapted to deliver a signal in the form of an electrical waveform containing information about the condition of said patient's heart;
    b. a waveform recognition and measurement device adapted to analyze said waveform and generate output based on said analysis; and
    c. a computer adapted to receive said output and calculate a numerical value representing said probability based on said output.

2. The device of claim 1, wherein said cardiovascular patient is primarily at risk for mortality due to acute myocardial infarction.

3. The device of claim 1, wherein said cardiovascular patient is primarily at risk for mortality due to congestive heart failure.

4. The device of claim 1 wherein the computer uses a regression formula to compute the probability from said output.

5. The device of claim 4 wherein the regression formula is of the form:

$$P = A[1 - (1 = e^Y)^{-1}],$$

$$Y = b_0 = \Sigma_{i=1 \to n} b_i X_i,$$

where

A is a positive number e equals the base of the natural log;

i is an integer index;

$b_o$ is a constant;

$X_i$, for i where $1 \leq i \leq n$, represent clinical variables, at lest some of which are determined by said output;

$b_i$ is regression coefficient corresponding to the $i^{th}$ clinical variable; and n is a positive integer representing the number of clinical variables used in the regression equation.

6. The device of claim 4 wherein the coefficients of the regression formula are derived from a reference population using stepwise regression analysis.

7. The device of claim 1 wherein the output includes information relating to the patient's ECG ST-segment.

8. The device of claim 7 wherein the output indicates whether the patient's ECG ST-segment is elevated.

9. The device of claim 7 wherein the output indicates whether the patient's ECG ST-segment is depressed.

10. The device of claim 1 wherein the output includes information relating to the patient's ECG T-waves.

11. The device of claim 10 wherein the output indicates whether the patient's ECG T-waves are elevated.

12. The device of claim 10 wherein the output indicates whether the patient's ECG T-waves are depressed.

13. The device of claim 1 wherein the output includes information relating to the patient's ECG Q-waves.

14. The device of claim 1 wherein the computer is adapted to also receive inputs relating to basic clinical data for the patient and to use said inputs along with said outputs to calculate the numerical value representing said probability.

15. The device of claim 14 wherein the basic clinical data inputs include the patient's age.

16. The device of claim 1 wherein the computer is adapted to also receive inputs relating to certain of the patient's vital signs and to use said inputs along with said outputs to calculates the numerical value representing said probability.

17. The device of claim 16 wherein the inputs relating to certain of the patient's vital signs include the patient's heart rate.

18. The device of claim 16 wherein the inputs relating to certain of the patient's vital signs include the patient's blood pressure.

19. A method for the assessment of cardiovascular mortality risk at a health care facility or provider comprising the steps of:

(a) providing the device of claim 1 to said health care facility or provider;

(b) using said device to calculate an individual predicted cardiovascular mortality risk of a patient at said health care facility or provider;

(c) repeating step (b) for a plurality of said patients, and using said individual predicted cardiovascular mortality risks to calculate a collective predicted cardiovascular mortality risk; and (d) adjusting the collective observed cardiovascular mortality rate for said facility or provider using said collective predicted cardiovascular mortality risk to yield a summary statistic representing the overall mortality risk at said facility or provider, or the risk adjusted mortality rate at said facility or provider.

20. The method of claim 19 wherein said individual predicted cardiovascular mortality risks conform substantially to a normal distribution, and may be characterized by a mean, called said collective predicted cardiovascular mortality risk, and a variance, and wherein said adjusted collective cardiovascular mortality rate is calculated by dividing said collective observed cardiovascular mortality risk by said collective predicted cardiovascular mortality risk, and multiplying the ratio so formed by a reference mortality rate.

21. The method of claim 20, wherein said reference mortality rate is a national statistic.

22. The method of claim 20, wherein said reference mortality rate is a regional or local statistic.

* * * * *

UNITED STATES PATENT AND TRADEMARK OFFICE
CERTIFICATE OF CORRECTION

PATENT NO. : 4,957,115
DATED : September 18, 1990
INVENTOR(S) : Harry P. Selker

It is certified that error appears in the above-identified patent and that said Letters Patent is hereby corrected as shown below:

Column 1, line 4:
   Please add before the "Background of the Invention", the following: --The Government has rights in this invention pursuant to Contract/Grant No. 5 R01 HS05549 awarded by the National Institutes of Health.--

Signed and Sealed this

Twenty-fifth Day of August, 1992

Attest:

DOUGLAS B. COMER

Attesting Officer          Acting Commissioner of Patents and Trademarks